US008710301B2

(12) United States Patent
Sawant et al.

(10) Patent No.: US 8,710,301 B2
(45) Date of Patent: Apr. 29, 2014

(54) METHOD FOR PRODUCING MALE STERILE PLANTS USING PLANT BECLIN 1/ATG6 EXPRESSION

(75) Inventors: Samir Vishwanath Sawant, Lucknow (IN); Rakesh Tuli, Lucknow (IN); Sudhir Pratap Singh, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 215 days.

(21) Appl. No.: 13/124,984

(22) PCT Filed: Nov. 26, 2009

(86) PCT No.: PCT/IB2009/007561
§ 371 (c)(1),
(2), (4) Date: Aug. 10, 2011

(87) PCT Pub. No.: WO2010/061276
PCT Pub. Date: Jun. 3, 2010

(65) Prior Publication Data
US 2011/0289631 A1    Nov. 24, 2011

(30) Foreign Application Priority Data

Nov. 28, 2008 (IN) .............................. 2697DEL2008

(51) Int. Cl.
*A01H 5/00* (2006.01)
*C12N 15/82* (2006.01)
*C12N 15/87* (2006.01)
*C12N 5/04* (2006.01)
*C12N 5/10* (2006.01)
*C12N 5/00* (2006.01)
*C12N 5/02* (2006.01)
*C12N 15/00* (2006.01)

(52) U.S. Cl.
USPC ........... 800/303; 800/287; 800/290; 435/468; 435/419; 435/430; 435/320.1

(58) Field of Classification Search
USPC .......................................................... 800/303
See application file for complete search history.

(56) References Cited

FOREIGN PATENT DOCUMENTS

WO    WO 99/23233 A1    5/1999

OTHER PUBLICATIONS

Terence A. Brown, Genomes Chapter 7 § 7.1.1; 7.2.1 (Oxford: Wiley-Liss) (2nd ed. 2002) available at http://www.ncbi.nlm.nih.gov/books/NBK21136/).*
Fujiki et al., An *Arabidopsis* Homolog of Yeast ATG6/VPS30 is Essential for Pollen Germination, 143 Plant Physiology, 1132-1139 (2007)).*
Qin et al., *Arabidopsis* AtBECLIN 1/AT6/AtVps30 is Essential for Pollen Germination and Plant Development, 17 Cell Research, 249-263 (2007).*

(Continued)

*Primary Examiner* — Cynthia Collins
*Assistant Examiner* — Rebecca Coobs
(74) *Attorney, Agent, or Firm* — Banner & Witcoff, Ltd.

(57) ABSTRACT

The present invention relates to a method for producing male sterile plants. It involves selective killing of reproductive cells in plants by using an autophagy related gene plant BECLIN I/ATG6. An expression cassette comprising plant BECLIN I/ATG6, regulated by a tapetum specific promoter can induce killing of tapetum cells. A particular area of interest is transforming a plant with said genetic construct and expression of the plant BECLIN I/ATG6 gene in tapetum at early stage of anther development to cause early collapse of tapetum to produce nonviable pollen, thus imparting male sterility in plants.

11 Claims, 2 Drawing Sheets

(56) References Cited

OTHER PUBLICATIONS

Harrison-Lowe and Olsen, Autophagy protein 6 (ATG6) is required for pollen germination in *Arabidopsis thaliana*, 4 Autophagy No. 3, 339-348 (2008).*

Kawanabe et al., Abolition of the Tapetum Suicide Program Ruins Microsporogenesis, 47 Plant Cell No. 6, 784-787 at 784 (2006).*

Goldberg et al., Anther Development: Basic Principles and Practical Applications, 6 Plant Cell, 1217-1229 at 1229, 1226-1227 (1993).*

Goldberg, Plants: Novel Developmental Processes, 240 Science No. 4858, 1460-1467 at Table 1 on p. 1461 (1988).*

Liu et al., Autophagy Regulates Programmed Cell Death during the Plant Innate Immune Response, 121 Cell, 567-577 (2005).*

Budar, F. et al., "Male sterility in plants: occurrence, determinism, significance and use," Comptes Rendus Des Seances de l'Academie Des Sciences; vol. 324, No. 6, Jun. 1, 2001, pp. 543-550.

Fujiki, Y. et al., "An *Arabidopsis* homolog of Yeast *ATG6*/VPS30 is Essential for Pollen Germination," Plant Physiology, vol. 143, No. 3, Mar. 2007, pp. 1132-1139.

Harrison-Lowe and Olsen, "Autophagy protein 6 (ATG6) is required for pollen germination in *Arabidopsis thaliana*," Autophagy, vol. 4, No. 3, Apr. 2008, pp. 339-348.

Qi, Chang-Qing et al., "Cloning and characterization of *Beclin1*-like gene in *Eupatorium odoratum* L. buds," Zhiwu Yanjiu/Bulletin of Botanical Research, vol. 28, No. 1, Jan. 1, 2008, pp. 67-72; with English Abstract.

Qin, Genji et al., "*Arabidopsis AtBECLIN 1/AtAtg6/AtVps30* is essential for pollen germination and plant development," Cell Research, vol. 17, No. 3, Mar. 2007, pp. 249-263.

* cited by examiner

```
                     SEQUENCE LISTING

<160> NUMBER OF SEQ ID NOS: 8

<210> SEQ ID NO 1
<211> LENGTH: 1554
<212> TYPE: DNA
<213> ORGANISM: Arabidopsis thaliana

<400> SEQUENCE: 1
atgaggaaag aggagattcc agataaaagt cggactatcc cgatcgatcc gaatctgccg      60
aaatgggtct gccaaaactg tcaccactcc cttaccatcg tcggcgtcga ttcctacgcc     120
ggcaagttct tcaacgatcc ccctccgtcc gctacgcagg gctcatctat ccatggagct     180
aacagtgttc ttggttcaac acgcatggac aactcttttg ttgttttacc tcgacataag     240
cctcctcaat ctcagggcat tcctccacgt cctcgcgggg cgtcctcacc tcagcctgat     300
```

```
gctactcaat ctggaaaggc gatggaggaa tcgtttgtag ttgtctataa gtctgagcct    360
gtttctgatt ctggtggttc tcacaatctg tctcttgaag tgggccaaaa cggtccctta    420
cattcaaata cttctggctt taatgcgact atcaatgtct taactcgtgc ttttgatatt    480
gctagaactc agacacaggt tgaacagcca ttgtgcttag aatgcatgag ggtattgtct    540
gataaacttg aaaagaagt cgaggatgtg acgagggacg tggaagcata cgaagcatgc    600
gttcagaggt tagaaggaga gacgcaagat gttcttagtg aagctgattt tctcaaggaa    660
aagaagaaga ttgaggaaga agaaagaaaa cttgttgcag ctatagaaga aacagagaaa    720
caaaatgctg aagtaaaacca tcaactgaag gagctagaat tcaagggaaa tcgttttaac    780
gaacttgaag atcggtattg gcaagagttc aataattttc agtttcaatt aattgcccat    840
caggaagaga gagatgcaat cttggcaaag attgaagttt cacaagcaca tttagagtta    900
ttaaataaga caaatgtact tattgatgcc ttccccatac ggaacgatgg ggaatttggt    960
acaattaaca attttcgact tggaagactc cctgccataa aagttgagtg ggatgagatc   1020
aatgctgctt ggggccaagc ctgtcttctc ctccatacga tgtgtaacta tttccggcca   1080
aagtttcaat gtcaagttaa aatacagccg atggggagtt atcctagaat tgtagacagc   1140
aacaacgaaa cttatgagct gtttggtcct gttaacttgt tttggagcac tcggtacgat   1200
aaagccatga cactgtattt gatgtgtctt aaagactttg ctgattttgc aaattcaaag   1260
gaccaagaga acaatattcc accagataat tgcctcaacc ttccatacaa gatcgaaaag   1320
gacaaagtat tggggtattc aataacacag agcttcaaca agcaagagag ttggaccaaa   1380
gcactaaagt atactctctg caacctcaaa tgggctctct actggttcgt tggaaacact   1440
aatttccaac ctctctctgc gacggtctct ctgccttcta atatatcagc ggctggttcc   1500
ttgtacgcca agcgaggtcc tgactctagt aagccttcat gtaaaaaaac ttag          1554

<210> SEQ ID NO 2
<211> LENGTH: 517
<212> TYPE: PRT
<213> ORGANISM: Arabidopsis thaliana

<400> SEQUENCE: 2

Met Arg Lys Glu Glu Ile Pro Asp Lys Ser Arg Thr Ile Pro Ile Asp
 1               5                  10                  15

Pro Asn Leu Pro Lys Trp Val Cys Gln Asn Cys His His Ser Leu Thr
                20                  25                  30

Ile Val Gly Val Asp Ser Tyr Ala Gly Lys Phe Phe Asn Asp Pro Pro
            35                  40                  45

Pro Ser Ala Thr Gln Gly Ser Ser Ile His Gly Ala Asn Ser Val Leu
        50                  55                  60

Gly Ser Thr Arg Met Asp Asn Ser Phe Val Val Leu Pro Arg His Lys
65                  70                  75                  80

Pro Pro Gln Ser Gln Gly Ile Pro Pro Arg Pro Arg Gly Ala Ser Ser
                85                  90                  95

Pro Gln Pro Asp Ala Thr Gln Ser Gly Lys Ala Met Glu Glu Ser Phe
            100                 105                 110

Val Val Val Tyr Lys Ser Glu Pro Val Ser Asp Ser Gly Gly Ser His
        115                 120                 125

Asn Leu Ser Leu Glu Val Gly Gln Asn Gly Pro Leu His Ser Asn Thr
    130                 135                 140

Ser Gly Phe Asn Ala Thr Ile Asn Val Leu Thr Arg Ala Phe Asp Ile
145                 150                 155                 160
```

-continued

```
Ala Arg Thr Gln Thr Gln Val Glu Gln Pro Leu Cys Leu Glu Cys Met
                165                 170                 175
Arg Val Leu Ser Asp Lys Leu Glu Lys Glu Val Glu Asp Val Thr Arg
            180                 185                 190
Asp Val Glu Ala Tyr Glu Ala Cys Val Gln Arg Leu Glu Gly Glu Thr
        195                 200                 205
Gln Asp Val Leu Ser Glu Ala Asp Phe Leu Lys Glu Lys Lys Lys Ile
    210                 215                 220
Glu Glu Glu Glu Arg Lys Leu Val Ala Ala Ile Glu Glu Thr Glu Lys
225                 230                 235                 240
Gln Asn Ala Glu Val Asn His Gln Leu Lys Glu Leu Glu Phe Lys Gly
                245                 250                 255
Asn Arg Phe Asn Glu Leu Glu Asp Arg Tyr Trp Gln Glu Phe Asn Asn
            260                 265                 270
Phe Gln Phe Gln Leu Ile Ala His Gln Glu Glu Arg Asp Ala Ile Leu
        275                 280                 285
Ala Lys Ile Glu Val Ser Gln Ala His Leu Glu Leu Leu Asn Lys Thr
    290                 295                 300
Asn Val Leu Ile Asp Ala Phe Pro Ile Arg Asn Asp Gly Glu Phe Gly
305                 310                 315                 320
Thr Ile Asn Asn Phe Arg Leu Gly Arg Leu Pro Ala Ile Lys Val Glu
                325                 330                 335
Trp Asp Glu Ile Asn Ala Ala Trp Gly Gln Ala Cys Leu Leu Leu His
            340                 345                 350
Thr Met Cys Asn Tyr Phe Arg Pro Lys Phe Gln Cys Gln Val Lys Ile
        355                 360                 365
Gln Pro Met Gly Ser Tyr Pro Arg Ile Val Asp Ser Asn Asn Glu Thr
    370                 375                 380
Tyr Glu Leu Phe Gly Pro Val Asn Leu Phe Trp Ser Thr Arg Tyr Asp
385                 390                 395                 400
Lys Ala Met Thr Leu Tyr Leu Met Cys Leu Lys Asp Phe Ala Asp Phe
                405                 410                 415
Ala Asn Ser Lys Asp Gln Glu Asn Asn Ile Pro Pro Asn Cys Leu
            420                 425                 430
Asn Leu Pro Tyr Lys Ile Glu Lys Asp Lys Val Leu Gly Tyr Ser Ile
        435                 440                 445
Thr Gln Ser Phe Asn Lys Gln Glu Ser Trp Thr Lys Ala Leu Lys Tyr
    450                 455                 460
Thr Leu Cys Asn Leu Lys Trp Ala Leu Tyr Trp Phe Val Gly Asn Thr
465                 470                 475                 480
Asn Phe Gln Pro Leu Ser Ala Thr Val Ser Leu Pro Ser Asn Ile Ser
                485                 490                 495
Ala Ala Gly Ser Leu Tyr Ala Lys Arg Gly Pro Asp Ser Ser Lys Pro
            500                 505                 510
Ser Cys Lys Lys Thr
        515
```

<210> SEQ ID NO 3
<211> LENGTH: 1000
<212> TYPE: DNA
<213> ORGANISM: Nicotiana tabacum

<400> SEQUENCE: 3
tccaacacca tttactccaa gggcactgta gtaaaaaaat aattaaatca tttttgaaat      60
ctaaaaaact cacttatttt ggaccataaa aaagggccaa aaaataact tattgtggac     120

```
cggagagagt aatacacttt ttggttagcg aatgcaatta atttagacat tgtgttatgt    180
tccagttaac cgcttccctg cacttctttc aatctatctc tcgatagaaa attgtgatac    240
tttgcgactt ctatcagagg acttttgtt ttccatgtaa caatctgtca ttttcgatgg    300
ggagatttgc acaaataggc tatttatgtg tcccaattta aattttaacc ccatgtcgat    360
cagaacttag ccacgagcac cagaagtttg atggatatgt gactttgtca ctatccggtt    420
tactaatcaa gagctatttt tattcaaaat tggatatcta gctaagtata actggataat    480
ttgcattaac agattgaata tagtgccaaa caagaaggga caattgactt gtcactttat    540
gaaagatgat tcaaacatga ttttttatgt actaatatat acatcctact cgaattaaag    600
cgacataggc tcgaagtatg cacatttagc aatgtaaatt aaatcagttt tgaatcaag     660 ctaaaagcag acttgcataa ggtgggtggc tggactagaa taaacatctt ctctagcaca    720
gcttcataat gtaatttcca taactgaaat cagggtgaga caaaattttg gtacttttc     780 ctcacactaa gtccatgttt gcaacaaatt aatacatgaa accttaatgt taccctcaga    840
ttagcctgct actccccatt ttcctcgaaa tgctccaaca aaagttagtt ttgcaagttg    900
ttgtgtatgt cttgtgctct atatatgccc ttgtggtgca agtgtaacag tacaacatca    960
tcactcaaat caaagttttt acttaaagaa attagctaaa                         1000

<210> SEQ ID NO 4
<211> LENGTH: 2849
<212> TYPE: DNA
<213> ORGANISM: Artificial Sequence
<220> FEATURE:
<223> OTHER INFORMATION: fusion between tapetum specific promoter and
      plant Beclin 1/ATG6 gene

<400> SEQUENCE: 4
ggatccagat cttccaacac catttactcc aagggcactg tagtaaaaaa ataattaaat     60 cattttgaa atctaaaaaa ctcacttatt ttggaccata aaaaaagggc caaaaaataa    120
cttattgtgg accggagaga gtaatacact ttttggttag cgaatgcaat taatttagac    180
attgtgttat gttccagtta accgcttccc tgcacttctt tcaatctatc tctcgataga    240
aaattgtgat actttgcgac ttctatcaga ggacttttg tttccatgt aacaatctgt     300 cattttcgat ggggagattt gcacaaatag gctatttatg tgtcccaatt taaattttaa    360
ccccatgtcg atcagaactt agccacgagc accagaagtt tgatggatat gtgactttgt    420
cactatccgg tttactaatc aagagctatt tttattcaaa attggatatc tagctaagta    480
taactggata atttgcatta acagattgaa tatagtgcca aacaagaagg gacaattgac    540
ttgtcacttt atgaaagatg attcaaacat gatttttat gtactaatat atacatccta    600
ctcgaattaa agcgacatag gctcgaagta tgcacattta gcaatgtaaa ttaaatcagt    660
ttttgaatca agctaaaagc agacttgcat aaggtgggtg gctggactag aataaacatc    720
ttctctagca cagcttcata atgtaatttc cataactgaa atcagggtga gacaaaattt    780
tggtactttt tcctcacact aagtccatgt ttgcaacaaa ttaatacatg aaaccttaat    840
gttaccctca gattagcctg ctactcccca ttttcctcga atgctccaa caaaagttag    900 ttttgcaagt tgttgtgtat gtcttgtgct ctatatatgc ccttgtggtg caagtgtaac    960
agtacaacat catcactcaa atcaaagttt ttacttaaag aaattagcta aatctagaat   1020
gaggaaagag gagattccag ataaaagtcg gactatcccg atcgatccga atctgccgaa   1080
atgggtctgc caaactgtc accactccct taccatcgtc ggcgtcgatt cctacgccgg   1140
caagttcttc aacgatcccc ctccgtccgc tacgcagggc tcatctatcc atggagctaa   1200
```

-continued

```
cagtgttctt ggttcaacac gcatggacaa ctcttttgtt gttttacctc gacataagcc    1260
tcctcaatct cagggcattc ctccacgtcc tcgcggggcg tcctcacctc agcctgatgc    1320
tactcaatct ggaaaggcga tggaggaatc gtttgtagtt gtctataagt ctgagcctgt    1380
ttctgattct ggtggttctc acaatctgtc tcttgaagtg ggccaaaacg gtcccttaca    1440
ttcaaatact tctggcttta atgcgactat caatgtctta actcgtgctt ttgatattgc    1500
tagaactcag acacaggttg aacagccatt gtgcttagaa tgcatgaggg tattgtctga    1560
taaacttgaa aaagaagtcg aggatgtgac gagggacgtg gaagcatacg aagcatgcgt    1620
tcagaggtta aaggagaga cgcaagatgt tcttagtgaa gctgatttc tcaaggaaaa    1680 gaagaagatt gaggaagaag aaagaaaact tgttgcagct atagaagaaa cagagaaaca    1740
aaatgctgaa gtaaaccatc aactgaagga gctagaattc aagggaaatc gttttaacga    1800
acttgaagat cggtattggc aagagttcaa taattttcag tttcaattaa ttgcccatca    1860
ggaagagaga gatgcaatct tggcaaagat tgaagtttca caagcacatt tagagttatt    1920
aaataagaca aatgtactta ttgatgcctt ccccatacgg aacgatgggg aatttggtac    1980
aattaacaat tttcgacttg gaagactccc tgccataaaa gttgagtggg atgagatcaa    2040
tgctgcttgg ggccaagcct gtcttctcct ccatacgatg tgtaactatt tccggccaaa    2100
gtttcaatgt caagttaaaa tacagccgat ggggagttat cctagaattg tagacagcaa    2160
caacgaaact tatgagctgt ttggtcctgt taacttgttt tggagcactc ggtacgataa    2220
agccatgaca ctgtatttga tgtgtcttaa agactttgct gattttgcaa attcaaagga    2280
ccaagagaac aatattccac cagataattg cctcaacctt ccatacaaga tcgaaaagga    2340
caaagtattg gggtattcaa taacacagag cttcaacaag caagagagtt ggaccaaagc    2400
actaaagtat actctctgca acctcaaatg ggctctctac tggttcgttg gaaacactaa    2460
tttccaacct ctctctgcga cggtctctct gccttctaat atatcagcgg ctggttcctt    2520
gtacgccaag cgaggtcctg actctagtaa gccttcatgt aaaaaaactt aggagctcga    2580
atttccccga tcgttcaaac atttggcaat aaagtttctt aagattgaat cctgttgccg    2640
gtcttgcgat gattatcata taatttctgt tgaattacgt taagcatgta ataattaaca    2700
tgtaatgcat gacgttattt atgagatggg ttttatgat tagagtcccg caattataca    2760
tttaatacgc gatagaaaac aaaatatagc gcgcaaacta ggataaatta tcgcgcgcgg    2820
tgtcatctat gttactagat cgggaattc                                      2849
```

<210> SEQ ID NO 5
<211> LENGTH: 33
<212> TYPE: DNA
<213> ORGANISM: Artificial Sequence
<220> FEATURE:
<223> OTHER INFORMATION: primer

<400> SEQUENCE: 5
ctagtctaga atgaggaaag aggagattcc aga    33

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
ctgcgagctc ctaagttttt ttacatgaag gctta    35

```
<210> SEQ ID NO 7
<211> LENGTH: 35
<212> TYPE: DNA
<213> ORGANISM: Artificial Sequence
<220> FEATURE:
<223> OTHER INFORMATION: primer

<400> SEQUENCE: 7
cgcggatcca gatcttccaa catttactcc aaggg                          35

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
cgtcgagctc ctaagttttt ttacatgaag gctta                          35
```

METHOD FOR PRODUCING MALE STERILE PLANTS USING PLANT BECLIN 1/ATG6 EXPRESSION

This application incorporates by reference an 11.8 kb text file created on Nov. 26, 2013 and named "12124984sequencelisting.txt," which is the sequence listing for this application.

FIELD OF INVENTION

The present invention relates to a method for producing male sterile plants. In particular this invention relates to transformation of a plant with said genetic construct comprising plant BECLIN 1 gene and expression of this gene in anther tapetum yields a male sterile transgenic plant. Male sterile plants are useful for the production of hybrid plants by sexual hybridization. The development of hybrid cultivars is highly desired because of their generally increased productivity due to increased hybrid vigor or heterosis.

BACKGROUND OF THE INVENTION AND PRIOR ART

Hybrid plants have become increasingly important in various commercial food crops around the world. Hybrid plants have the advantages of higher yield, better quality and stress resistance than their parents, because of heterosis or hybrid vigor. Crop uniformity is another advantage of hybrid plants when the parents are homozygous; this leads to improved crop management. Hybrid seed is therefore commercially important and sells at a premium price. In crops such as maize, sunflower, sorghum, sugar beet, cotton, and many vegetables, hybrids account for a large share of the seed market. Not only the USA and Europe, but also many developing countries rely on their food production to a large extent on hybrids. Sale of hybrids in various crops account for nearly 40 percent of the global commercial seed business of about US$ 15 billion. This share is likely to increase as the importance of hybrid vigor is yet to be realized fully, especially in developing countries.

The production of hybrid varieties of maize (from the thirties in the US), cotton (since 1970 in India) and of rice (since 1976 in China) represents the most significant and successful breeding efforts of the twentieth century. A 6-fold increase was observed between 1930 and 1990 for US corn yield after the introduction of hybrid breeding, compared to uniform performances for selected open pollinated populations during the previous 60 years (Stuber, 1994).

The concept of hybrid vigor ((Zirkle, 1952)) emerged since the early observations in the eighteenth century by J. G. Koelreuter of interspecific crosses in *Nicotiana, Dianthus, Verbascum, Mirabilis, Datura*, confirmed by Darwin (Darwin, 1876) in vegetables, and W. J. Beal in maize (Beal, 1880). Subsequently, this effect was exploited in plant breeding (Shull, 1952) when the tools to produce the necessary amount of seeds became available in hermaphrodite species: the first male sterility system was developed in onion in 1943 (Jones, 1943) and others were developed in a wide range of species such as sugar beet, maize, sorghum, sunflower, rice, rapeseed, carrot (Frankel, 1977).

The key to the successful commercial production of hybrid seeds is sufficient control of the pollination process that is male sterility. Male sterility is defined as the failure of plants to produce functional anthers, pollen, or male gametes. First documentation of male sterility came in 1763 when Kolreuter observed anther abortion within species and specific hybrids.

Maize has distinctly separate male and female flowers which makes the plant well suited to manual or mechanical emasculation. The tassels are removed from the seed plants before they are able to shed pollen. Even though detasseling is currently used in hybrid seed production for plants such as maize, the process is labor-intensive and costly, both in terms of the actual detasseling cost and yield loss as a result of detasseling the female parent.

Most major crop plants of interest have both functional male and female organs within the same flower, therefore, emasculation is not a simple procedure. While it is possible to remove by hand the pollen forming organs before pollen is shed, this form of hybrid production is extremely labor intensive and expensive. Seed is produced in this manner only if the value and amount of seed recovered warrants the effort.

A1

Another general means of producing hybrid seed is to use chemicals that kill or block viable pollen formation. These chemicals, termed gametocides, are used to impart a transitory male-sterility. Commercial production of hybrid seed by use of gametocides is limited by the expense and availability of the chemicals and the reliability and length of action of the applications. A serious limitation of gametocides is that they have phytotoxic effects, the severity of which is dependent on genotype. Other limitations include that these chemicals may not efficiently reach the mail reproductive parts or may not be effective for crops with an extended flowering period because new flowers produced may not be affected. Consequently, repeated application of chemicals is required.

Many current commercial hybrid seed production systems for field crops rely on a genetic means of pollination control. Plants that are used as females either fail to make pollen, fail to shed pollen, or produce pollen that is biochemically unable to affect self-fertilization. Of more widespread interest for commercial seed production are systems of pollen-control-based genetic mechanisms causing male sterility. There are three main types of male sterility observed in nature. All three types of male sterility are used in commercial breeding programs to ensure cross-pollination to produce hybrid seeds in different crops.

One type of male sterility is nuclear encoded called as genetic male sterility. It is ordinarily governed by a single recessive gene, ins but dominant genes governing male sterility are also known e.g. in sunflower. Thus nuclear male sterility can be either dominant or recessive. Many different nuclear male sterile (ms) genes have been isolated in maize. In rice 25 ms are known. In a plant homozygous recessive for such a gene, the pollen fails to develop to maturity. For breeding purposes, a recessive male-sterile parent plant is maintained by crossing it with a heterozygous male-fertile plant that also includes the recessive male-sterility allele, so that the offspring are 50% recessive male-sterile plants. The other 50% are male-fertile plants that have to be rogued out in outcrossing programs which can only be done efficiently if the recessive male-sterility allele is segregated together with a selectable or screenable marker. In U.S. Pat. No. 4,727,219, a procedure is described for the use of recessive male sterility for the production of, hybrid maize. Dominant nuclear male sterile plants, as compared to recessive male sterile plants, can be maintained through crossing with a male-fertile plant, to produce offspring that are 50% dominant male-sterile plants. The usefulness of dominant nuclear male-sterile plant is, however, limited because its dominant male-sterility allele is in most cases not tightly linked (i.e., within the same genetic locus) to a selectable or screenable marker. Dominant sterility can only be used for hybrid seed formation if propagation of the female line is possible (for example, via in vitro clonal propagation). Dominant nuclear male-sterile lines were developed with a blue seed marker in durum and common wheat (Tian and Liu, 2001). This genetic male sterility is of wide occurrence in plants but commercial utility of this sterility system is limited by the expense of clonal propagation and roguing the female rows of self-fertile plants.

Genetic male sterility may be subdivided into two broad groups: (1) environment insensitive i.e. ins gene expression is much less affected by environment and (2) environment sensitive i.e. ins gene expression occurs within specific range of temperature and/or photoperiod regimes; this type of sterility is known in rice, tomato, wheat etc. The environment sensitive male sterility is further divided into two groups (1) temperature sensitive genetic male sterility e.g. rice TGMS line Pei-Ai645 and (2) photoperiod sensitive genetic male sterility e.g. rice 5047S. In addition approaches in genetic engineering have been used to produce transgenic male sterility, for which a novel approach is discussed in this document.

The second type of male sterility is conditioned by hereditary particles in the cytoplasm. Cytoplasmic male sterility is caused by the extranuclear genome (mitochondria or chloroplast) and shows maternal inheritance. Manifestation of male sterility in these may be either entirely controlled by cytoplasmic factors or by the interaction between cytoplasmic and nuclear factors. They show non-Mendelian inheritance. This is not a very common type of male sterile system in the plant kingdom. Cytoplasmic male sterility (CMS) of the seed line can be achieved through crossing with naturally occurring CMS germplasm as female parent. Here the sterility is transmitted only through the female and all progeny will be sterile. This is not a problem for crops such as onions or carrots where the commodity harvested from the F1 generation is produced during vegetative growth. But in other cases where clonal propagation is not possible CMS lines must be maintained by repeated crossing to a sister line (known as the maintainer line) that is genetically identical except that it possesses normal cytoplasm and is therefore male fertile. This approach of induction of male sterility in the seed line on the basis of sterilizing cytoplasm was employed in rice, sorghum, sunflower and millet. But the offspring of plants of this type are only of commercial value if the economic product of the offspring is not for use as seed but rather for plants such as ornamentals and sugarbeet.

When nuclear genes for fertility restoration (Rf) are available for CMS system in any crop, it is called as cytoplasmic genetic male sterility (CGMS). The restorers of fertility (Rf) genes are distinct from genetic male sterility genes. This third type male sterility system is the result of a combination of both nuclear encoded male sterility and cytoplasmatically encoded male sterility. Here sterility is manifested by the influence of both nuclear and cytoplasmic genes. The cases of cytoplasmic male sterility would be included in the cytoplasmic-genic system as and when restorer genes for them would be discovered. It is likely that a restorer gene would be found for all the cases of cytoplasmic male sterility if thorough search were made. There are commonly two types of cytoplasms, N (normal) and S (sterile). The Rf genes do not have any expression of their own unless the sterile cytoplasm is present. Rf genes are required to restore fertility in S cytoplasm which causes sterility. Thus a combination of N cytoplasm with rfrf and S cytoplasm with Rf-produces fertiles; while S cytoplasm with Of produces only male steriles. N cytoplasm with Rfrf is best for stable fertility. U.S. Pat. No. 6,320,098 described a method of producing cytoplasmic-genetic male sterile soybean and method for producing hybrid soybean. U.S. Pat. No. 5,773,680 utilized cytoplasmic-genetic male sterility system in the production of hybrid wild rice.

Generally, the use of CMS for commercial seed production involves maintenance of three breeding lines: a male-sterile line (female parent), a maintainer line which is isogenic to the male-sterile line but contains fully functional mitochondria and a restorer line which has nuclear genes (Rf genes) for fertility restoration.

Discovery of dominant negative genes which would alter plant development would be particularly useful in developing genetic methods to induce male sterility because other available methods, including cytoplasmic male sterility and nuclear male sterility have shortcomings. A dominant negative gene is one that, when expressed, effects a dominant phenotype in the plant. Herskowitz (1987), used the term "dominant negative" to denote a gene that encodes a mutant polypeptide which, when over-expressed, disrupts the activity of the wild-type gene. A wild type gene is one from which the mutant derived. In the present description the dominant negative gene is applied to a gene coding for a product that disrupts an endogenous genetic process of a host cell which receives the gene, and that is effective in a single copy or may produce an effect due to overexpression of the gene either by increased production of the gene product. Exemplary of the class of dominant negative genes are cytotoxic genes, methylase genes, and growth-inhibiting genes. Dominant negative genes include diphtheria toxin A-chain gene (Czako and An, 1991), cell cycle division mutants such as CDC in maize (Colasanti, et al., 1991) the WT gene (Farmer, et al., 1994) and P68 (Chen, et al., 1991). Biotechnology has enabled the development of several new pollination control systems that could be useful for hybrid seed production. Since the first transgenic male sterility system was described (Mariani, 1990), many strategies to produce male-sterile plants have been reported. There has been significant interest in using an ablation system for controlling reproductive development in plants. Reproductive control has been achieved in several plant species by genetic ablation, which entails linking a reproductive-preferred promoter with a dominant negative gene to ablate reproductive cells. Prior art regarding the proposed invention are as follows:

Patents EP344029, EP1135982 and WO89/10396 described a system for producing a male sterile plant by transforming a plant with a DNA encoding barnase under the control of a tapetum-specific promoter. Barnase is an RNase originating in *Bacillus amyloliquefaciens*. This enzyme has 110 amino acid residues and hydrolyzes RNA. When expressed in cells, this enzyme degrades RNA in cells and thus inhibits the functions of the cells and finally causes cell death in many cases. By using this characteristic, it is therefore expected that the function of the specific site can be selectively controlled by expressing the barnase gene in a specific site of a plant. Transformation of tobacco and oilseed rape plants with such a promoter-gene construct prevented the plants from producing fertile pollen (Mariani et al., 1990). Similarly collapse of tapetum was also observed when A9 and A6 promoters were used to drive expression of the barnase gene in transgenic plants (Hird et. al., 1993; Paul et. al., 1992).

When the barnase gene was employed as a male sterility gene, however, it was frequently observed that resulting male sterile transgenic plants exhibit unfavorable characteristics. PCT International Publication WO96/26283 refers to this problem in rice. It is also reported that similar phenomena are observed not only in rice but in lettuce (Reymaerts et. al., 1993). Patent Application 20020166140 reported mutated barnase gene at least in part and then the thus obtained mutant barnase gene, having a weakened effect was anther-specifically expressed in a plant so as to make the plant substantially male sterile without any substantially disadvantageous effect on the tissues other than anthers. In this patent production of male sterile plants, free from any unfavorable characteristic at a high efficiency was claimed.

U.S. Pat. No. 5,763,243, U.S. Pat. No. 6,072,102, U.S. Pat. No. 5,792,853, U.S. Pat. No. 5,837,851 and U.S. Pat. No. 5,795,753 have used a DNA adenine methylase (DAM) gene, isolated from *E. coli* as a dominant negative gene. Changes in the DNA methylation pattern of specific genes or promoters have accounted for changes in gene expression. Methylation of DNA is a factor in regulation of genes during development of both plants and animals. Methylation patterns are established by methods such as the use of methyl-sensitive CpG-containing promoters (genes). In general, actively transcribed sequences are under methylated. In animals, sites of methylation are modified at CpG sites (residues). Genetic control of methylation of adenine (A) and cytosine (C) (nucleotides present in DNA) is affected by genes in bacterial and mammalian species. In plants, however, methyl moieties exist in the sequence CXG, where X can be A, C or T, where C is the methylated residue. Inactivation due to methylation of A is not known in plants, particularly within GATC sites known to be methylated in other systems. *E. coli* DNA adenine methylase (DAM) for which GATC is a target inactivates a genetic region critical for pollen formation or function thereby causing a male sterile plant to form.

Patent E P0942965, U.S. Pat. No. 6,177,616 and U.S. Pat. No. 6,384,304 used DNA molecules which code for deacetylases or proteins having the biological activity of a deacetylase. These molecules can be used to produce plants having parts which can be deliberately destroyed i.e. plants which have male sterility, by the specific expression of a deacetylase gene (Kriete et. al. 1996, Bartsch 2001). The deacetylase genes from *Streptomyces viridochromogenes* [N-acetyl-L-phosphinothricyla-lanylalanine (N-acetyl-PTT) deacetylase, dea] and argE from *Escherichia coli* (N-acetyl-L-ornithine deacetylase) encode proteins having specificity for N-acetyl-L-PPT. For both genes, it was possible in the case of tapetum-specific expression in plants to show the occurrence of male-sterile flowers after treatment of individual buds with N-acetyl-L-PPT. For successful use of this system, in particular in the treatment of whole plants with N-acetyl-PPT under practically relevant conditions, it is advantageous to be able to employ deacetylases having high substrate affinity. Therefore further deacetylases having high affinity for N-acetyl-PPT were sought. In U.S. Pat. No. 6,177,616 and U.S. Pat. No. 6,384,304 N-acetyl-PPT deactylase gene from *Stenotrophomonas* sp. was used for the production of male sterile plants.

Patent E P0455690, reported a method of inhibiting respiration of a plant cell by use of a gene, which is expressible in anthers of plants, to inhibit mitochondrial function leading to cell death and failure to produce viable pollen, thus imparting male sterility. The disrupter gene was selected from the mammalian uncoupling protein (UCP) cloned from mammalian (usually rat) brown adipose tissue. The proposed disrupter protein, UCP, is instrumental in the thermogenesis of mammalian brown adipose tissue and exists as a dimer in the mitochondrial inner membrane forming a proton channel and thus uncoupling oxidative phosphorylation by dissipation of the proton electrochemical potential differences across the membrane.

U.S. Pat. No. 5,254,801, reported a phosphonate monoesterase gene (pehA), found suitable for purpose such as inducing male sterility for hybrid seed production in plants. A bacterial phosphonate monoester hydrolase was evaluated in plants as a conditional lethal gene useful for cell ablation and negative selection. A phosphonate monoesterase gene (pehA) encoding an enzyme that hydrolyzes phosphonate esters including glyceryl glyphosate to glyphosate and glycerol was cloned from the glyphosate metabolizing bacterium, *Burkholderia caryophilli* PG2982. As an example of tissue-specific cell ablation, floral sterility without vegetative toxicity was demonstrated by expressing the pehA gene using a tapetum specific promoter and treating the mature plants with glyceryl glyphosate. (Dotson et. al. 1996).

WO 99/04023 proposed a method of controlling fertility of plants by the use of DNA molecule that encodes avidin, a glycoprotein. High level expression of avidin gene in anthers can induce male sterility. Avidin, a glycoprotein has a very strong affinity for biotin (vitamin H) with a $K_D$ (dissociation constant) of approximately $10^{-15}$ M$^{-1[1]}$, the highest known affinity between any protein and its ligand. This binding is essentially irreversible. Fertility can be restored by spraying the plant with a solution of biotin.

U.S. Pat. No. 5,955,653 discovered a tapetum-specific callase (beta.-1,3-glucanase) gene, designated A6, from *Brassica napus* and other members of the family Brassicaceae including *A. thaliana*. The A6 gene encodes a 53 kDa callase enzyme of *Brassica napus* and equivalent proteins in other Brassicaceae family members. Coding sequence from the gene can be driven by an appropriate promoter to induce male sterility in plants. Microspore release is the process by which the immature microspores are liberated from a protective coat of .beta. (1,3) poly-glucan (callose) laid down by the microsporogenous cells before meiosis (Rowley, (1959); Heslop-Harrison (1968)). The anther-expressed glucanase responsible for the dissolution of this callose coat is known as callase. Callase is synthesised by the cells of the tapetum and secreted into the locule. The appearance of the enzyme activity is developmentally regulated to coincide precisely with a specific stage of microspore development. The basis of the use of a glucanase as a sterility DNA lies in the fact that mis-timing of the appearance of callase activity is associated with certain types of male-sterility (Warmke and Overman, 1972). One important attraction of glucanase as a potential sterility DNA is that it already occurs in a natural system. But the timing of the appearance of callase activity is critical.

U.S. Pat. No. 7,230,168 described transformation of a plant cell with a nucleic acid construct encoding cytokinin oxidase where expression of the cytokinin oxidase inhibits pollen formation or male organ development in the transgenic plant. Fertility restoration in the plant may be achieved after restoration of normal cytokinin levels by application of cytokinins or cytokinin oxidase inhibitor such as a cytokinin oxidase 1 inhibitor. Hear ability of the particular cytokinin oxidase to oxidatively remove cytokinin side chains to give adenine and the corresponding isopentenyl aldehyde was utilized to create male sterility.

In animal systems, studies of apoptosis have revealed pathways where proteins of the Bcl-2 family play key roles. The Bcl-2 family includes pro-apoptotic (e.g. Bax, Bak and Bid) and anti-apoptotic (e.g. Bcl-2, Bcl-xl and Ced-9) members that appear to control the initiation of apoptosis through mitochondria (Gross et al. 1999). A Bax gene has been shown to induce PCD in plant cells (Lacomme and Cruz 1999, Kawai-Yamada et al. 2001). A mouse Bax gene was connected to the tapetum-specific promoter, expression of the Bax gene caused cell death resulting pollen abortion (Tsuchiya et al. 1994, Ariizumi et al. 2002). A suppressor of Bax-induced cell death has been identified in plants. Expression of AtBI-1, a homolog of mammalian Bax inhibitor, in the tapetum at the tetrad stage inhibits tapetum degeneration and subsequently results in pollen abortion, while activation of AtBI-1 at the later stage does not (Patent JP2006345742-A, Kawanabe et. al. 2006).

Diphtheria toxin A chain (DTA) gene was expressed in tapetum which resulted in dominant male sterility due to the specific cell ablation (Koltunow et. al., 1990). Similarly, when the S-locus glycoprotein gene promoter of Brassica was fused to the DTA gene and transferred into tobacco (Thorness et al., 1991) and *A. thaliana* (Thorness et al 1993) it resulted in self-sterile plants due to expression of gene in both pistil and anthers. APETALA3 (AP3) promoter-DTA fusion resulted in the complete ablation of petals and stamen in transgenic tobacco (Day et. al., 1995). Temperature sensitive diphtheria toxin A chain (DTA) gene was also used to confer conditional male sterility in *Arabidopsis thaliana* (Guerineau F et. al., 2003).

O'Kefee et al (1994) described R7402/P450sU1 system in which P450SU1 (*Streptomyces* griseolus gene encoding herbicide-metabolizing cytochrome) expression and R7402 treatment can be used as a negative selection system in plants. In tobacco expressing P450SU1 from a tapetum-specific promoter, treatment of immature flower buds with R7402 caused dramatically lowered pollen viability. Such treatment could be the basis for a chemical hybridizing agent. This may provide a strategy for development of a chemical male sterilant for hybrid seed production.

A ribosome inactivating protein (RIP) from *D. sinensis* was used as a cytotoxic gene to induce male sterility in tobacco plants (Cho H J et. al. 2001). Ribosome inactivating protein inactivates eukaryotic ribosomes and inhibits general protein synthesis. Actually it inhibits its own protein synthesis (Boness et. al. 1994). Due to its suicidal action it was proposed to use in genetic cell ablation and genetic improvement by Cho H J.

Hofig et. al. (2006) expressed a stilbene synthase gene (STS) in anthers of transgenic *Nicotiana tabacum* plants, resulting in complete male sterility in 70% of transformed plants. The grapevine stilbene synthase (STS) has been shown to compete with the enzyme chalcone synthase (CHS) for the substrates malonyl-CoA and coumaroyl-CoA. STS-induced sterility in tobacco is believed to result from a reduced or abolished flavonol biosynthesis. This has been confirmed by experiments where STS-sterile tobacco plants were regularly sprayed with flavonols and where fertility was partially restored. STS, when expressed in non-tapetal cells, is not expected to have a toxic impact since there is no competing CHS present.

Autophagy is a ubiquitous process in eukaryotic cells, in which portions of the cytoplasm are sequestered in double-memberane vescicles for delivery to a degradative organelle, vacuole or lysosome (Reggiori et. al. 2002). Autophagy is known to be active at basal levels under normal physiological conditions; it can be stimulated by a plethora of stresses including cellular damage, nutrient starvation and pathogen infection (Levine and Klionsky, 2004). It is well established that autophagy promotes cell survival during nutrient starvation by degrading and recycling nutrients (Seay M. et. al. 2006). AuTophaGy-related (ATG) genes are essential for autophagosome formation. In the last decade, with the identification of approximately 30 ATG genes in *Saccharomyces cerevisiae* and other fungi (Klionsky et. al. 2003), the molecular mechanisms of autophagy have gradually been elucidated ((Klionsky et. al. 2005). Autophagy is conserved across all eukaryotes and homologs of many yeast ATG genes have recently been identified in various eukaryotic systems, and the molecular mechanisms of autophagy are also conserved (Yang Cao et. al. 2007). Autophagosome formation is a complex process and each Atg protein has been shown to function at specific stage during autophagosome formation in the yeast (Tsukada et. al. 1993). A number of Atg proteins accumulate to a perivacuolar structure termed the pre-autophagosomal structure (PAS) (Kim et. al. 2002). Among the ATG genes, ATG6 is relatively unique in its not being autophagy-specific (Yang Cao et. al. 2007). For example, the *S. cerevisiae* ATG6/VPS30 gene product is the only protein required for both autophagy and sorting of the vacuole resident hydrolase carboxypeptidase Y through the Vps pathway (Kametaka et. al. 1998). Yeast Atg6/Vps30 is a subunit of two distinct class III phosphotidylinositol (PtdIns) 3-kinase complexes pathways (Kihara et. al. 2001). Complex I functions in autophagy, whereas complex II is involved in Vps, which explains why Atg6/Vps30 participates in both, otherwise separate, pathways.

BECLIN 1, the mammalian homologue of yeast ATG6 was the first identified mammalian gene with a role in mediating autophagy (Liang et. al., 1999). BECLIN 1 was originally discovered during the course of a yeast two-hybrid screen of a mouse brain cDNA library using human Bcl-2 as the bait (Liang et. al. 1998). Overexpression of Human BECLIN 1 prompts autophagic cell death in human MCF7 breast carcinoma cells (Liang et. al., 1999). Recently BECLIN 1 was found to participate in apoptosis signaling through caspase-9 thus BECLIN 1 may be the critical 'molecular switch' and play an important role to fine tune autophagy and apoptosis (Wang et. al. 2007). BECLIN 1 is conserved in higher eukaryotes. Human Beclin 1 protein shares 36% identity and 52% similarity with *Nicotiana* Beclin 1 (Liang et. al., 1999).

If a plant is to survive an infection, hypersensitive response (HR) cell death (PCD) must be carefully controlled so that it does not spread throughout the plant and kill it. The plant ortholog of BECLIN 1 was first studied in *Nicotiana benthamiana* plants (Liu Y. et. al. 2005) and it was found essential for restriction of HR PCD during disease resistance (Seay M. et. al. 2006, Liu Y. et. al. 2005, Patel S. et. al. 2006). Plants deficient in the plant BECLIN 1 exhibit unrestricted HR PCD in response to pathogen infection (Liu Y. et. al. 2005). Autophagosomes were rarely observed in the cells of plant BECLIN 1 silenced plants after infection with TMV (Liu Y. et. al. 2005). Autophagosomes are induced at the site of TMV infection during HR PCD and plant BECLIN 1/ATG6 is required for induction of autophagy in both pathogen infected cells and uninfected adjacent cells to restrict HR PCD at infected site (Liu Y. et. al. 2005). Thus there is a prodeath signal(s) moving out of the pathogen-infected area into adjacent tissues and distal sites that is negatively regulated by autophagy. These findings provide the genetic evidence that ATG genes can function in vivo as a negative regulator of HR PCD. These results contrast with findings from mammalian studies in which ATG genes are required to promote PCD in cells lacking intact apoptotic machinery (Liu Y. et. al. 2005).

Recently, it was reported that AtBECLIN 1/ATG6 in plants has distinct function in addition to autophagy: vesicle trafficking and pollen germination (Fujiki Y. et. al. 2007, Qin G. et. al. 2007). They reported that deletions of AtBECLIN 1/ATG6 specifically influenced male gametophytes but not the female reproductive structures. Pollens lacking AtBECLIN 1/ATG6 failed to germinate. During pollen germination and pollen tube growth, cellular trafficking is critical for cell wall deposition and cell shape remodeling (Parton R M et. al. 2003, Parton R M et. al. 2001, and Helper P K et. al. 2001). It is possible that ATG6 deletions alter the cellular trafficking system which results failure of pollen germination (Qin G. et. al. 2007). AtBECLIN 1/ATG6 deficient plants displayed retarted growth, dwarfism and early senescence this suggests that AtBECLIN 1/ATG6 is required for normal plant development (Qin G. et. al. 2007).

Tapetum is the innermost sporophytic layer of anther wall and surrounds the microspores. The tapetum is known to provide nutrition to developing microspores especially exine of pollen grains, the main structural components of the pollen wall. The tapetum degenerates during the later stages of pollen development. It has been speculated that tapetum degeneration is a programmed cell death (PCD) event (Wu and Cheun 2000). [Nuclei of tapetum cells and the tissues of anther wall were found TUNEL (terminal deoxynucleotidyl transferase mediated dUTP nick end labeling) positive by Wang et. al. (1999).] The proper timing of cell death in the tapetum is essential for normal microsporogenesis. Kawanabe et. al. (2006) had shown that expression of mouse Bax gene in tapetum at early stage of pollen development can cause early degeneration of tapetum resulting into pollen abortion.

In the present invention, AtBECLIN 1/ATG6 gene is being expressed in tapetum in stage 2 and 3 of pollen development (which has not been previously reported). This causes disruption of normal cell death programme of tapetum and there is a delay in the induction of tapetal programmed cell death (PCD). Hence, pollen formed are abnormal having an intact tapetum, resulting in male sterility.

OBJECTS OF THE INVENTION

The main object of the present invention is to provide a method for producing male sterile plants by expressing plant BECLIN 1 gene in the tapetum layer of anthers during early stages of pollen development.

Another object of the present invention is to provide a method, wherein the expression of BECLIN 1 gene in the tapetum disrupts the normal cell death programme of tapetum, resulting in abnormal pollen having intact tapetum.

Another object of the present invention is to provide an expression vector comprising the expression cassette $TA_{29}BECLIN$ 1 which is a useful tool for generating male sterile lines of various crop plants.

Another object of the present invention is to provide an expression vector capable of introducing said expression cassette $TA_{29}BECLIN$ 1 into a plant cell genome when placed in *Agrobacterium* infected plant cells.

Yet another object of the present invention is to induce male sterility by causing transformation in plants selected from a group consisting of tobacco, cotton, rice, wheat, corn, potato, tomato, oilseed rape, alfalfa, sunflower, onion, clover, soyabean, pea.

Yet another object of the present invention is to obtain seeds of male sterile crop plants.

Yet another object of the present invention is to use a gene product of plant origin for induction of male sterility in plants, which circumvents the biosafety problems associated with expressing other bacterial, viral, mammalian proteins for the same purpose.

Still another object of the present invention is to express BECLIN 1 gene which codes for a non-cytotoxic polypeptide, hence does not pose any problems if leakage into other cells occurs.

SUMMARY OF THE INVENTION

Accordingly, the present invention provides a method for producing male sterile plants by expressing plant BECLIN 1 gene in the tapetum layer of anthers during early stages of pollen development.

In an embodiment of the present invention, the method comprises the steps of:
a) Detaching the third and fourth rosette leaves of about 3 week old *Arabidopsis thaliana* plants and floating them on deionized water in Petri dishes, adaxial side up;
b) incubating the rosette leaves obtained in step (a) at 22±1° C. in the dark for about 48 hours to artificially induce autophagy;
c) extracting total RNA from autophagy induced leaves obtained in step (b) as herein described;
d) preparing cDNA from total RNA extracted in step (c) by known methods;
e) amplifying plant BECLIN 1/ATG6 gene from cDNA prepared in step (d) using gene specific primers by PCR;
f) cloning the amplified plant BECLIN 1/ATG6 gene obtained in step (e) in a vector as herein described;
g) constructing an expression cassette by gene fusion between tapetum specific promoter having Seq ID no. 3 and plant Beclin 1/ATG6 gene having Seq ID no. 1 obtained from step (f) and Nos terminator sequence in a cloning vector;
h) sub-cloning the expression cassette as constructed in step (g) into a binary vector as herein described;
i) introducing the resultant binary vector of step (h), carrying the said expression cassette, into *Agrobacterium tumefaciens*;
j) transforming the plant in which male sterility is to be induced with recombinant *Agrobacterium tumefaciens* obtained in step (i);
k) developing independent transgenic lines.

In an another embodiment of the invention wherein transformation is carried out in plants selected from a group consisting of tobacco, cotton, rice, wheat, corn, potato, tomato, oilseed rape, alfalfa, sunflower, onion, clover, soyabean, pea.

In yet another embodiment of the invention wherein plant, cell, tissue are obtained by the above mentioned process.

In yet another embodiment of the invention a recombinant vector useful for inducing male sterility in plants by transformation comprising of:
i. an anther specific promoter;
ii. a plant BECLIN 1 gene;
iii. a Nos terminator sequence;

In yet another embodiment of the invention the anther specific promoter used is a tapetum specific promoter, represented by SEQ ID NO: 3.

In yet another embodiment of the invention the plant BECLIN 1 gene having SEQ ID NO: 1 and codes for a polypeptide having SEQ ID NO: 2 or its homologue.

In yet another embodiment of the invention the expression cassette comprises a chimeric gene fusion between tapetum specific promoter and plant Beclin 1/ATG6 gene is having the polynucleotide sequence represented by SEQ ID NO: 4.

In yet another embodiment of the invention a plant, cell, tissue is transformed with the recombinant vector as mentioned above.

In yet another embodiment of the invention it provides a transgenic plant expressing/overexpressing plant BECLIN 1 gene in its anther.

In yet another embodiment of the invention the method is used for inducing male sterility in plants listed above.

In yet another embodiment of the invention use of the recombinant vector for inducing male sterility in plants listed above.

In yet another embodiment of the invention it provides a kit for inducing male sterility in plants comprising of
a. A vector having an anther specific promoter and a plant BECLIN 1 gene;
b. Suitable reagents;
c. Instruction manual.

BRIEF DESCRIPTION OF THE FIGURES

FIGS. 1A and 1C, pollen of control plants. FIGS. 1B and 1D, pollen of transgenic plants.

DETAILED DESCRIPTION OF THE INVENTION

Figure 1:
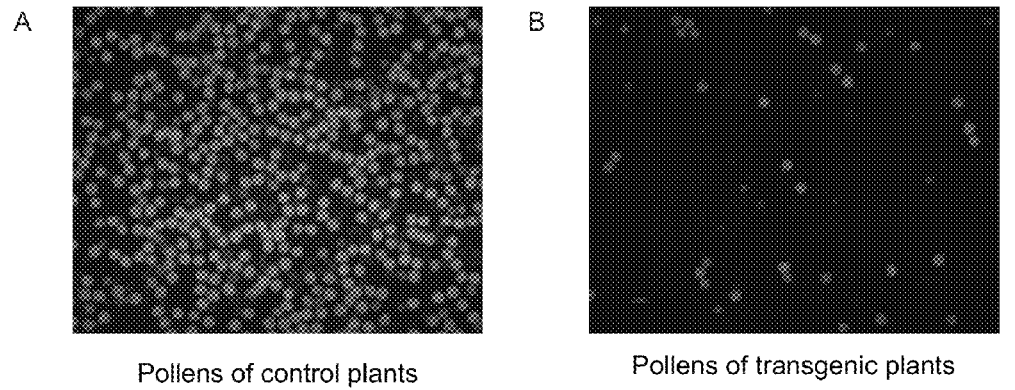
FIGS. 1A-D. Results of fluorochromatic reaction (FCR) test (showing pollen viability) and in vitro pollen germination test.
Figure 1:
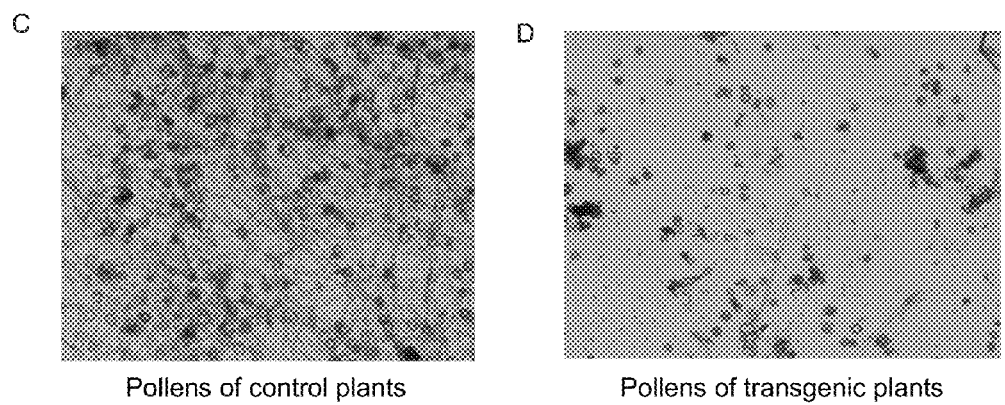

The present invention relates to a method for producing male sterile plants by expressing plant BECLIN 1 gene in the tapetum layer of anthers during early stages of pollen development.

It also relates to the use of AtBECLIN 1/ATG6 gene in the induction of male sterility in plants. In the present invention, AtBECLIN 1/ATG6 gene is being expressed in tapetum in stage 2 and 3 of pollen development. This causes disruption of normal cell death programme of tapetum and there is a delay in the induction of tapetal programmed cell death (PCD). Hence, pollen formed are abnormal, having an intact tapetum, resulting in male sterility. Most of the transgenic lines showed severely reduced pollen production as compared to the wild type tobacco plants. The pollens produced were deformed and most of them were empty. Even in vitro pollen germination assay, pollen grains of these transgenic lines failed to germinate and those which germinated showed short pollen tubes.

This is for the first time it has been demonstrated that expression of plant autophagy related gene (ATG6 gene) in anther cells can cause the male sterility. We report that the expression of plant BECLIN 1/ATG6 gene, driven by a suitable promoter expressed in tapetum at an appropriate stage results in male sterility in transgenic tobacco.

The present invention provides a recombinant construct for transforming plants to confer male sterility, wherein the expression cassette comprises regulatory sequence operably linked to a polynucleotide sequence, plant BECLIN 1/ATG6 as shown in SEQ ID NO: 1 or a functional variant thereof. The invention also relates to a method of producing transgenic plants having plant parts which can be destroyed specifically after expressing said gene. Further, the invention provides a method for producing male sterile transgenic plants by expressing said gene product in tapetum.

In the present invention the term of male sterility in plants indicates about 90-100% sterility with 0-10% viable pollen production in anthers.

A "cloning vector" is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide antibiotic or herbicide resistance.

An "expression cassette" is a DNA molecule comprising a gene that is expressed in a host cell and a promoter, driving its expression. Typically, gene expression is placed under the control of certain tissue-specific regulatory elements.

The term "expression" refers to the biosynthesis of a gene product. For example, in the case of a structural gene, expression involves transcription of the structural gene into mRNA and the translation of mRNA into one or more polypeptides.

A "recombinant vector" is a vector in which a foreign DNA has been inserted.

An "expression vector" is a vector in which an expression cassette has been genetically engineered.

A "binary vector" is able to replicate in both *E. coli* and *Agrobacterium tumefaciens*. It typically contains a foreign DNA in place of T-DNA, the left and right T-DNA borders, marker for selection and maintenance in both *E. coli* and *Agrobacterium tumefaciens*, a selectable marker for plants. This plasmid is said to be disarmed since its tumor-inducing genes located in the T-DNA have been removed.

A "suitable promoter" includes a tissue-specific or cell-specific promoter that controls gene expression in those particular cells of a particular tissue. An "anther-specific promoter" is a DNA sequence that directs a higher level of transcription of an associated gene in anther tissue than in some or all other tissues of a plant. In present invention suitable promoter directs expression only in cells that are critical for the formation or function of pollen, including tapetum cells, pollen mother cells, and early microspores.

A "functional variant of plant BECLIN 1/ATG6" is a variant which retains the autophagy inducing property and have 80% similarity of nucleotide sequence as shown in SEQ ID NO: 1 and amino acid sequence as shown in SEQ ID NO: 2.

The following examples are set forth as representative of specific and preferred embodiments of the present invention, and should not be construed so as to limit the scope of the invention.

EXAMPLE 1

Isolation of a cDNA Encoding BECLIN 1/ATG6 Gene from *Arabidopsis*

Plant material: The ecotype Columbia (Col-0) of *Arabidopsis thaliana* was used throughout the experiments described here. Plants were grown on a compound soil mixture of vermiculite/peat moss/perlite (1:1:1) in a growth chamber with a light cycle of 16 h light/8 h dark and a temperature cycle of 23° C. day/18° C. night.

Artificial induction of autophagy: The third and fourth rosette leaves of 3 week old plants were detached and floated on deionized water in Petri dishes, adaxial side up. Leaves were incubated at 22±1° C. in the dark for 48 hours.

Cloning of plant BECLIN 1/ATG6 gene: Total RNA was extracted from autophagy induced leaves of *Arabidopsis* by TRI Reagent (Sigma). The amount of total RNA was measured by NANODROP® ND-1000 UV-Vis Spectrophotometer. The quality of RNA was checked by visualizing the rRNA in ethidium bromide-coloured agarose gel under UV light. Ten micrograms of total RNA was used in cDNA preparation. cDNA was generated using SUPERSCRIPT® Reverse Transcriptase kit (Invitrogen) following the manufacturer's instructions. The cDNA was used as template to amplify plant BECLIN 1/ATG6 gene by using one set of primers, 5'-ctagtctagaatgaggaaagaggagattccaga-3' (SEQ ID NO:5) 5'-ctgcgagctcctaagttttttacatgaaggctta-3' (SEQ ID NO:6). The PCR reaction consisted of 30 cycles 94° C. for 30 sec, 58° C. for 30 sec and 72° C. for 90 sec. The PCT product of 1.5 kb was cloned in pBluescript SK+ vector (Stratagene, La Jolla, CAlif.). Nucleotide sequence of the cloned PCR product was determined by using BIGDYE® Terminator v3.1 Cycle Sequencing Kit (Applied Biosystems). Sequence homology was analyzed using BLAST program.

EXAMPLE 2

Construction of Chimeric Gene Fusion Between Tapetum Specific Promoter and Plant BECLIN 1/ATG6

An early stage, tapetum specific 1 kb BamH1/Xba1 promoter was fused with 1.5 kb Xba1/Sac1 plant BECLIN 1 gene and 250 bp Sac1/EcoR1 Nos terminator in BamH1/EcoR1 Sk+ Cloning vector.

The entire expression cassette containing fragments BamH1/EcoR1 was further sub-cloned into binary vector pBI101. The resultant pBI101 carrying the expression cassette was into *Agrobacterium tumefaciens* strain LBA4404 following the modified protocol (Cangelosi et al., 1991).

EXAMPLE 3

Transformation of Tobacco Plants

As described in Example 2, recombinant *Agrobacterium tumefaciens* carrying the expression cassette was used for transformation of *Nicotina tabacum* cv. Petit Havana by protocol as described by Horsch et al., in 1985.

In short a single isolated colony of *A. tumefaciens* LBA 4404 harboring binary vector with above described expression cassettes was inoculated in YEP medium containing antibiotics streptomycin (250 µg/ml) rifampicin (50 µg/ml) and kanamycin (100 µg/ml) and grown (200 rpm, overnight, 28° C.). Fifty micro liters of the overnight culture was diluted to 100 ml in YEP medium and grown till $OD_{600}$ reached to 0.8. Cells were recovered by centrifugation in SS34 rotor (5,000 rpm, 10 min, 4° C.). The pellet was suspended in co-cultivation medium (MS salts, 2% glucose, 10 mM MES and 100 mM acetosyrengone, pH 5.6) to $OD_{600}$ 0.6. Tobacco leaf discs were co-cultivated with *A. tumefaciens* for two days in dark. After co-cultivation, the leaf discs were transferred to regeneration medium supplemented with cefotaxime (250 µg/ml) and kanamycin (100 µg/ml). The culture was incubated at 25 with 16 hrs light and 8 hrs dark cycle for a period of four weeks. After this, the transgenic shoots were harvested and transferred to rooting medium containing kanamycin (50 µg/ml). After incubation for 2-4 weeks, the putative transgenic plantlets were transferred to Hoagland solution for acclimatization and then transferred to vermiculite for hardening for three weeks. The plants were transferred from vermiculite to soil in glasshouse. Independent transgenic lines were developed for the expression cassette (chimeric gene fusion).

EXAMPLE 4

Analysis of Transgenic Lines for Transgene Integration

Genomic DNA of the transgenic lines and control plant was isolated by CTAB method of DNA extraction. The genomic DNA was used as template to amplify a fragment of 2.5 kb comprising TA29 promoter and plant BECLIN 1 gene by using one set of primers, 5'-cgcggatccagatcttccaacatt-tactccaaggg-3' (SEQ ID NO:7) and 5'-cgtcgagctcctaagttttt-tacatgaaggctta-3' (SEQ ID NO:8). The PCR reaction consisted of 94° C. for 4 min, 94° C. for 1 min, 60° C. for 1 min and 72° C. for 2 min, Go to 2 for 30 cycles 72° C. for 5 min. The desired band of 2.5 kb was obtained in the PCR of transgenic lines and positive control but not in control plants and negative control (without template). This experiment was repeated for three times for confirmation.

EXAMPLE 5

Analysis of Transgenic Lines for Male Sterility

The transgenic plants grew well to visible maturity and showed normal flowering. Expression of the autophagy gene in anthers did not lead to any morphological abnormalities except nonviable pollens and very poor or no seed setting. Thus the transgenic plants were male sterile. Pollen viability was evaluated by fluorescein diacetate staining (Heslop-Harrison, 1970). Pollen samples were collected at blooming time and their quality was tested by the fluorocromatic procedure (FCR), which principally tests the integrity of the plasmalema of the vegetative cell. This integrity seems to be closely correlated with viability. Most of the pollens of the transgenic plants were not viable. As shown in Table 1, plants of three transgenic lines had 5 to 14% viable pollen, rest of the pollens of the plants were not showing fluorescence (FIGS. 1A-D). On the other hand control plants (Independent transgenic lines for an expression cassette comprising GUS reporter gene driven by tapetum specific promoter), showed 80to 92% pollen viability (Table 2, FIGS. 1 A-D)

Invitro pollen germination test was performed using artificial liquid media proposed by Kwack (1964). Extensive pollen germination was observed in the cultured pollens of one anther of control plants (Independent transgenic lines for an expression cassette comprising GUS reporter gene driven by tapetum specific promoter) however pollens of transgenic lines either failed to germinate or if germinated showed severely retarded pollen tube growth. In the transgenic plants (Independent transgenic lines for the expression cassette comprising plant BECLIN 1/ATG6 gene driven by tapetum specific promoter) of four different lines 0-1% pollen germination was observed in comparison to 62-75% in control plants (Table 1 & Table 2).

Figure 2:
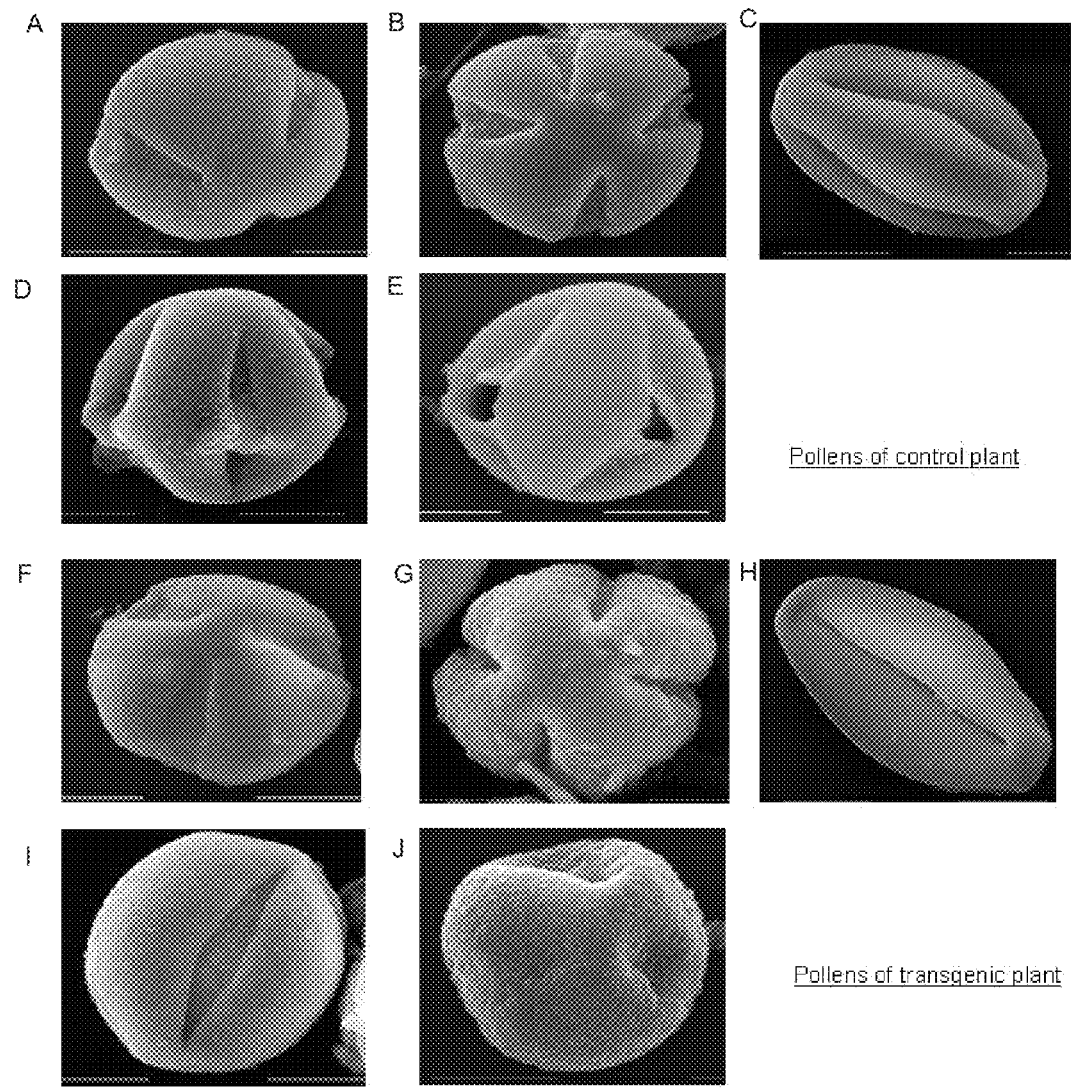
FIGS. 2A-J. Scanning electron micrographs of pollens in control plants (FIGS. 2A, 2B, 2C, 2D, 2E) and transgenic plants (FIGS. 2F, 2G, 2H, 2I, and 2J).

Further, pollen grains were observed under scanning electron microscopy. The pollen grains of transgenic lines showed difference in sculpturing pattern of exine and lack of germ pores (FIGS. 2 A-J).

Fruit set was normal in the transgenic plants of all the six lines but the bulbs were of smaller size. Seed setting was severely affected in bulbs of the transgenic plants. Seed weight per pod of the transgenic plants of twelve different lines was nil to 32.07 mg whereas in control plants it was 36.6 mg to 113.34 mg (Table 3 & Table 4).

TABLE 1

Evaluation of pollen viability and pollen germination

| Transgenic Lines* | Pollen Viability % | Pollen Germination % |
|---|---|---|
| 1354 (1) | 2~6 | 0~0.03 |
| 1354 (2) | 2~7 | 0~0.09 |
| 1354 (3) | 9~14 | 0~1 |
| 1354 (4) | 5~8 | 0~0.06 |
| 1354 (5) | 7~10 | 0~0.08 |
| 1354 (6) | 7~12 | 0~0.18 |

*Independent transgenic lines for the expression cassette comprising plant BECLIN 1/ATG6 gene driven by tapetum specific promoter as claimed in claim 6.

TABLE 2

Evaluation of pollen viability and pollen germination

| Transgenic Lines* | Pollen Viability % | Pollen Germination % |
|---|---|---|
| 1351 (1) | 85~90 | 65~75 |
| 1351 (2) | 80~90 | 65~70 |
| 1351 (3) | 80~92 | 62~71 |
| 1351 (4) | 84~96 | 72~77 |
| 1351 (5) | 80~92 | 74~79 |
| 1351 (6) | 81~96 | 73~77 |

*Independent transgenic lines for an expression cassette comprising GUS reporter gene driven by tapetum specific promoter.

TABLE 3 seed setting

| Transgenic Line* | Seed Weight (gm) | Total Number of Pods | Seed Weight Per Pod (mg) |
|---|---|---|---|
| 1354 (1) | Nil | 9 | Nil |
| 1354 (2) | 0.0522 | 37 | 1.41 |
| 1354 (3) | 0.7102 | 42 | 13.9 |
| 1354 (4) | Nil | 23 | Nil |
| 1354 (5) | 0.210 | 18 | 11.6 |
| 1354 (6) | 0.822 | 49 | 16.7 |

TABLE 3-continued seed setting

| Transgenic Line* | Seed Weight (gm) | Total Number of Pods | Seed Weight Per Pod (mg) |
|---|---|---|---|
| 1354 (7) | 0.102 | 9 | 11.3 |
| 1354 (8) | 0.091 | 23 | 3.95 |
| 1354 (9) | 0.370 | 28 | 13.21 |
| 11354 (10) | 0.834 | 26 | 32.07 |
| 1354 (11) | 0.228 | 10 | 22.8 |
| 1354 (12) | 0.658 | 68 | 9.67 |

*Independent transgenic lines for the expression cassette comprising plant BECLIN 1/ATG6 gene driven by tapetum specific promoter.

TABLE 4

Seed setting

| Control* | Seed Weight (gm) | Total Number of Pods | Seed Weight Per Pod (mg) |
|---|---|---|---|
| 1351 (1) | 1.7382 | 45 | 38.62 |
| 1351 (2) | 0.3815 | 6 | 63.58 |
| 1351 (3) | 1.7134 | 29 | 59.08 |
| 1351 (4) | 1.9002 | 29 | 65.08 |
| 1351 (5) | 0.440 | 12 | 36.6 |
| 1351 (6) | 0.336 | 7 | 48.07 |
| 1351 (7) | 1.064 | 12 | 88.67 |
| 1351 (8) | 1.182 | 17 | 69.52 |
| 1351 (9) | 0.680 | 6 | 113.34 |
| 1351 (10) | 2.085 | 22 | 94.77 |
| 1351 (11) | 1.21 | 11 | 110.36 |
| 1351 (12) | 0.5 | 7 | 71.42 |

*Independent transgenic lines for an expression cassette comprising GUS reporter gene driven by tapetum specific promoter.

ADVANTAGES OF THE INVENTION

1. The expression vector claimed in this invention is a good tool for generating male sterile lines of various crop plants.
2. It is advantageous to use plant BECLIN1/ATG6 as male sterility gene because it has no product which is cytotoxic outside the target cell.
3. The plant BECLIN1/ATG6, as a male sterility DNA mimics natural systems and is inherently less destructive than for example ribonuclease, diphtheria toxin and so does not present such a problem if 'leakage' occurs into other cells.

We claim:

1. A method for producing a male sterile plant, comprising expressing a plant BECLIN 1/ATG6 gene in the tapetum layer of anthers during early stages of pollen development, thereby obtaining a male sterile plant.

2. The method as claimed in claim 1, comprising the steps of:
   a. detaching the third and fourth rosette leaves of an about 3 week old *Arabidopsis thaliana* plant and floating the third and fourth rosette leaves on deionized water in Petri dishes, adaxial side up;
   b. incubating the third and fourth rosette leaves obtained in step (a) at 22±1° C. in the dark for about 48 hours to artificially induce autophagy-induced third and fourth rosette leaves;
   c. extracting total RNA from the autophagy—induced third and fourth rosette leaves obtained in step (b) as herein described;
   d. preparing cDNA from the total RNA extracted in step (c);
   e. amplifying the plant BECLIN 1/ATG6 gene from cDNA prepared in step (d) using gene specific primers by PCR;
   f. cloning the amplified plant BECLIN 1/ATG6 gene obtained in step (e) in a vector;
   g. constructing an expression cassette by gene fusion between a tapetum specific promoter having SEQ ID NO:3 and the plant BECLIN 1/ATG6 gene having SEQ ID NO:1 obtained from step (f) and the plant Nos terminator sequence in a cloning vector;
   h. sub-cloning the expression cassette as constructed in step (g) into a binary vector;
   i. introducing the resultant binary vector of step (h), carrying the said expression cassette, into *Agrobacterium tumefaciens*;
   j. transforming a plant in which male sterility is to be induced with recombinant *Agrobacterium tumefaciens* obtained in step (i);
   k. developing an independent transgenic line of the plant.

3. The method as claimed in claim 1, wherein the plant is selected from the group consisting of tobacco, cotton, rice, wheat, corn, potato, tomato, oilseed rape, alfalfa, sunflower, onion, clover, soybean, and pea.

4. A male sterile plant obtained by the method of claim 1.

5. A plant cell or tissue obtained from the male sterile plant of claim 4.

6. A recombinant vector, comprising a chimeric gene fusion consisting of:
   i. an anther specific promoter, wherein the anther specific promoter is a tapetum specific promoter represented by SEQ ID NO:3;
   ii. a polynucleotide sequence that codes for a polypeptide having SEQ ID NO:2; and
   iii. a Nos terminator sequence.

7. The recombinant vector as claimed in claim 6, wherein the chimeric gene fusion comprises the polynucleotide sequence represented by SEQ ID NO:4.

8. The recombinant vector as claimed in claim 6, wherein the polynucleotide sequence comprises SEQ ID NO:1.

9. A plant comprising a tapetum layer wherein the plant comprises a recombinant vector and wherein the recombinant vector comprises a chimeric gene fusion consisting of:
   i. an anther specific promoter, wherein the anther specific promoter is a tapetum specific promoter represented by SEQ ID NO:3;
   ii. a polynucleotide sequence that codes for a polypeptide having SEQ ID NO:2; and
   iii. a Nos terminator sequence.

10. A plant cell or tissue obtained from the plant of claim 9.

11. A kit, comprising:
   a. a recombinant vector comprising a chimeric gene fusion consisting of:
      i. an anther specific promoter, wherein the anther specific promoter is a tapetum specific promoter represented by SEQ ID NO:3;
      ii. a polynucleotide sequence that codes for a polypeptide having SEQ ID NO:2; and
      iii. a Nos terminator sequence;
   b. suitable reagents; and
   c. instructions for a method for producing a male sterile plant, comprising expressing a plant BECLIN 1/ATG6 gene in the tapetum layer of anthers during early stages of pollen development, thereby obtaining a male sterile plant.

* * * * *

UNITED STATES PATENT AND TRADEMARK OFFICE
CERTIFICATE OF CORRECTION

PATENT NO. : 8,710,301 B2
APPLICATION NO. : 13/124984
DATED : April 29, 2014
INVENTOR(S) : Sawant et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 286 days.

Signed and Sealed this
Twenty-ninth Day of September, 2015

Michelle K. Lee
*Director of the United States Patent and Trademark Office*